(12) United States Patent
Tan et al.

(10) Patent No.: US 11,866,714 B2
(45) Date of Patent: Jan. 9, 2024

(54) PROMOTER FOR YEAST

(71) Applicant: BASF SE, Ludwigshafen (DE)

(72) Inventors: Xuqiu Tan, San Diego, CA (US); Ruorong Cai, San Diego, CA (US); Jingping Zhong, San Diego, CA (US); Melissa Ann Scranton, San Diego, CA (US); Michael Speer, San Diego, CA (US)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/734,682

(22) PCT Filed: Jun. 3, 2019

(86) PCT No.: PCT/US2019/035140
§ 371 (c)(1),
(2) Date: Dec. 3, 2020

(87) PCT Pub. No.: WO2019/236451
PCT Pub. Date: Dec. 12, 2019

(65) Prior Publication Data
US 2021/0254082 A1 Aug. 19, 2021

Related U.S. Application Data

(60) Provisional application No. 62/682,053, filed on Jun. 7, 2018.

(51) Int. Cl.
*C12N 15/81* (2006.01)
*C07K 14/39* (2006.01)

(52) U.S. Cl.
CPC ............ *C12N 15/815* (2013.01); *C07K 14/39* (2013.01)

(58) Field of Classification Search
CPC .................................................... C07K 14/39
See application file for complete search history.

(56) References Cited

U.S. PATENT DOCUMENTS

2019/0300889 A1* 10/2019 Nishi ....................... C12N 5/10

FOREIGN PATENT DOCUMENTS

| EP | 2862933 A2 | 4/2015 |
|---|---|---|
| WO | WO-2006/089329 A2 | 8/2006 |
| WO | WO-2012/129036 A2 | 9/2012 |
| WO | WO-2013/050551 A1 | 4/2013 |
| WO | WO-2016/139279 A1 | 9/2016 |

OTHER PUBLICATIONS

Küberl, A.., et al. 2011 Journal of Biotechnology 154: 312-320. (Year: 2011).*
Macauley-Patrick, S., et al. 2005 Yeast 22: 249-270. (Year: 2005).*
Lambertz, C., et al. 2014 Biotechnology for Biofuels 7:135 (15 pages). (Year: 2014).*
Jr. McGehee, et al., "Differentiation-specific element: a cis-acting developmental switch required for the sustained transcriptional expression of the angiotensinogen gene during hormonal-induced differentiation of 3T3-L1 fibroblasts to adipocytes", Molecular Endocrinology, vol. 7, Issue 4, Apr. 1, 1993, pp. 551-560.
Lemaigre, et al., "Transcriptional control of genes that regulate glycolysis and gluconeogenesis in adult liver", Biochemical Journal, vol. 303 (Pt 1), Oct. 1, 1994, pp. 1-14.
Mary R. Loeken, "Effects of mutation of the CREB binding site of the somatostatin promoter on cyclic AMP responsiveness in CV-1 cells", Gene Expression: The Journal of Liver Research, vol. 3, Issue 3, 1993, pp. 253-264.
Needleman, et al., "A general method applicable to the search for similarities in the amino acid sequence of two proteins", Journal of Molecular Biology, vol. 48, Issue 3, Mar. 28, 1970, pp. 443-453.
O'Reilly, et al., "Identification of an activating transcription factor (ATF) binding site in the human transforming growth factor-beta 2 promoter", Journal of Biological Chemistry, vol. 267, Issue 28, 1992, pp. 19938-19943.
R. Treisman, "The SRE: a growth factor responsive transcriptional regulator", Seminars in Cancer Biology, vol. 1, Issue 1, Feb. 1, 1990, pp. 47-58.
Ye, et al., "Characterization of a silencer regulatory element in the human interferon-gamma promoter", Journal of Biological Chemistry, vol. 269, Issue 41, Oct. 14, 1994, pp. 25728-25734.
García-Ortega, et al., "Rational development of bioprocess engineering strategies for recombinant protein production in Pichia pastoris (Komagataella phaffii) using the methanol-free GAP promoter. Where do we stand?", New Biotechnology, vol. 53, 2019, pp. 24-34.
International Search Report for PCT Patent Application No. PCT/US2019/035140, dated Aug. 26, 2019, 7 pages.
Prielhofer, et al., "Induction without methanol: novel regulated promoters enable high-level expression in Pichia pastoris", Microbial Cell Factories, vol. 12, Issue 1, Jan. 24, 2013, 10 pages.
Shen, et al., "A novel methanol-free Pichia pastoris system for recombinant protein expression", Microbial Cell Factories, vol. 15, Issue 1, 2016, 11 pages.
Wang, et al., "Methanol-Independent Protein Expression by AOX1 Promoter with trans-Acting Elements Engineering and Glucose-Glycerol-Shift Induction in Pichia pastoris", Scientific Reports, vol. 7, Feb. 2, 2017, 12 pages.
Berg et al., "Combinatorial Mutagenesis and Selection to Understand and Improve Yeast Promoters", BioMed Research international, May 2013, 9 pages.
Mordaka et al., "Stringency of Synthetic Promoter Sequences in Clostridium Revealed and Circumvented by Tuning Promoter Library Mutation Rates", ACS synth, Bio., Jan. 2018, 7:672-681.

* cited by examiner

*Primary Examiner* — Marsha Tsay
(74) *Attorney, Agent, or Firm* — DLA Piper LLP (US)

(57) ABSTRACT

A promoter operably linked to a gene encoding a protein is disclosed. The promoter drives expression of the protein in a yeast cell in the absence of methanol. Also disclosed are vectors, host cells and expression systems that include the promoter, as well as methods of using the promoter to express proteins in yeast.

23 Claims, 6 Drawing Sheets

Specification includes a Sequence Listing.

SEQUENCE LISTING

<160> NUMBER OF SEQ ID NOS: 7

<210> SEQ ID NO 1
<211> LENGTH: 1501
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1
tccagtgtag cactaaaatc taatatcttc ggctttatac ttttttgttc atccgaaagc     60
ttacgaacaa ttctttctcc tgttttattg tggatataga caatttcgtc agtttcttgg    120
agagaagagt tatttccggt tttggctggc cctataaacg ggttcttgga tttggatcta    180
gtaataaaaa tgtcactgtc attctcggag ctgaactttg tgttgtacga agatgggttg    240
ttccactgtt ttgccagctc ttcattgatg attttcttag tgggtgttct tggaggttca    300
cgttgcctat aatcttgacg ttcttcttca tcactatcga tgccatcaaa attaagcgtc    360

```
cttattgcag gcttttgtga tttcaactgc aatccttcta tctcttcatc agagctttcg    420
aactgaatac tatcactcaa aactggcgac attgcacatt tccgcaaacc atttcgggaa    480
tctatgctag ctcttctaga cgataaagaa cgaccggaac caatacgggg ttgtgcaggt    540
gggaataaat atgttggttt ggattcttga cgtgaagaag gtattctagt cgatgaagtg    600
gttgataagg atatggcgtc actgagttgt tttcttttcc tatgttgcgg tgttgggtca    660
ggagttaatt gattcacctc cataactctg gaatttcttg aatgtggggt tttcagatgg    720
gcatctttct tgacggggtt gtgagtaacg gaggaacctg gtgtcttggg tgtgaacggt    780
gtttgagcct gtacgcggtt acttctgggc ggagtactcg gagtcatgag agccattgat    840
tagaaggtga atgagggagt caccactcta agcaaacaaa atgaggtcga agcaaaaaat    900
aaagtaaagt agcacttctg gcaggttaga tcaaagagtg acgggagatt tgaagatggc    960 tggttttttcc ttagtcttgg aagaggtttg tgtgggtatc agcgaatatt ccccgattag   1020
gcaaattagt tgcattgaaa ttaacacgac atggtgattt gtggtaacaa atatctattg    1080
gtggttggtg tgtgggtgta atagtggtcg tgtcatgatg atggtgttca ggtgttgtca    1140
tagatcggtc ttcagtaaga gaaggaagct tggtgacgat cacagctatg atgtaataga    1200
aattgctaag caattgtgag gtgtgatgta ttttgcagag caattgtgcg gtacaacggg    1260
gtgttattgt cttcacaagg catttattgc gaatttcgta gttgaaagaa tattttagca    1320
cagggtgctt gacccctatt gttgctcgct aaaccatgat tgctaaatga tgacatagca    1380
atcactttac taagattgct ataaggacac ctttcttagt ataaatggac actctttttcc    1440 cctgctaaac ttcttttatt tttcacactt aaacagttac aaaacacaaa cacaactaga    1500
a                                                                   1501
```

<210> SEQ ID NO 2
<211> LENGTH: 1501
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 2

```
gtgctaaaat ctgaggttta caagctgtga tgttccccta agatctcaca atcgaacaat     60
cgcgaagcca atgcaagttg tttaaggggga aacgactcac tattcctgaa attagtattc    120
aaaacttggt ccggaagaac aatgaggcgg ccgttaaaat actcacgtaa acggtgtcta    180
caagcgcatt aaaatccgtt tgaattcaag caaaagccac cagaggctta tgcttggtta    240
tacccagcat tgacctttgg tatgagcatc tgaaaaacaa ccaggtgttg caaagttaaa    300
catccttctt tgttcatata gaacccacta ttcatggtac tccccaatcg aatttcacat    360
tctggttttg aaattacaca ccacgttagc ttataagatt tcatataact tattgatata    420
cggtttccat tgttcgaata gttgaggttg tatgtaattc gattgaaggg gccattttttg    480 tttcctactt ttcctgggag cttatccgat gcgcttcaaa gctggaattg taaatataga    540
gaaaaagaag gatgttgttt tattcttgaa agagtataat tttacttcta gcaactctcc    600
cacttcgctt gacttcatt atttcttggg cacataggcg tagtaatcta gaccaacaga    660
taatttgccg gaatgatata gcgattggaa aatgaactga aatttttttgc tgtctttcaa    720 tttgacgggc agttcatcag tgaccgacca tataaatacg ttgagaatgt tattcttcct    780
cgtagttgaa gtggcttcat aatttcagaa ctcaatagat aaactaggat gttttaaagc    840
```

```
aattaatgct cacaagtaag gagcgactct cttgcttttc gaatactaaa agtatcgtcc    900
caacccagaa aaaagacct cttaactgca aaataaactc tatatatttc ttctaaaaca     960
gtttcaggtt ggatagtatc gcattctcat cacttctaac tagtaggcca tgagatatat   1020
taacgtttac ttgagttcta agttctccga attagatgca cagcacaaac aagattaggt   1080
ttcacttggt acaaaatacg aacagagttt aaggtcgtaa tttcatttcg ttattgatcc   1140
ccacaatcta ttcttatcac agtcatcaga tagtcgcgaa aaagcatgca gaaaaggggg   1200
tcgtccctat ctaagttgta gcattacaac aaatatgact acactcagtg tcgcaatcgg   1260
tatagccaac gctgcaaaat ggattctact gagaatggta tgatgatccc aggatcaatt   1320
tcccaaaaat taaaaaagt aaaataaaaa gcatcagata ttagggaggt ggtaagattg    1380
ctctgcaagc gatcacgaga ttttaggttt tcctttatgt actatataaa gcgcagattg   1440
gatgccgctt ttccctcctg ggctatgata atatagcgaa cgaaatacac gccaaaataa   1500
a                                                                  1501
```

<210> SEQ ID NO 3
<211> LENGTH: 1500
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 3

```
tcacattcat agcatctctc gcctgcaata gcttccacga taggaatatc tgtgaaagtg     60
aacatgctat ttcgatgata taagacttta agatctggca tgtttgtgtt ggaggttacc    120
ctggggtcaa taaccctaat tatctccttc actaaaaatg atgaagattc ttcggattcg    180 ttttttgaaca gagttaatgc catttcttcg tcaatagaaa aatcaatatc tggtatctca   240
tcttttacat attgaggatt tagttttctt ccctttggat agtacattat gatcaatgta    300
ttcctgtctt tattgataaa gtattggcat tctgcttctt gtcacccttt gaattgtttg    360
tctggaagtg actgacattt ttccacattg ctaacggttt ggcacgaatt acatctaaat    420
aaaatgtctt ctccggattc gtgtattaag tgatactcca atgataaatc cccacctatc    480
gaaccagaat cggcattggc cacagtcaca ggtaacttta ggtcttgaaa atccttcta    540 taggcttcat tgacattgtc ataagactta agaccatctt ctttggtcaa gtcaaaagaa    600
taggcatctt tcatgagaaa ctctcgtcct ctcaacaaac ctcccctagg tctcaactca    660
tctctatatt tgcgggaaat ttggtacacg agaaggggta atctttata tgacgaacat     720 aagtcaccaa ctaagtttgt gatttcctct tcacaagttg gcactaaaca gtagtctcta    780
tccttggagt ctttgaactt gaacaattca ttgttgtccc atctcttagt tctctcccat    840
aaatgcttgg aagacaggct acttaattcc atttccagcc caccagcctg atccattctt    900
ttcctaatta cattttgaag ctttttatag gtacggagtc ctaatggaag ccagtgaact    960
attcctgctg caggctggta aataaacctt gattgaagga gcatatcatg agtagtaagg   1020 tccttttacag aaaatagttt acttccttga agagaagtag aataaaacct catgttgggt  1080
ctccatgaaa ggttcaaagg cattgatcct ttaggtactt caggatgttt aagtcatcaa   1140
actgtccatc aaaggtagta tagtatttac catctagata gtgatgtatg ggtgtaacac   1200
aacatttaaa tgttgtaaat taacattagg actgagtccg gagatgctat tgtcacctaa   1260
atctattaga aagcacttca gttatatcat cgatagaggt ttgaagataa acctattgtt   1320
```

-continued

```
gataaataac cccattaccc gtttacgtag caaggttcaa aaatttgctt agatcggagc 1380
taaaaattcg actgacttct ttcgaaaatg tggattatgc aagcaacgtt gctatcggaa 1440
tagtatataa ggtcgatctg ccccattaca aattgtaaag caacaaacat cctacgcaaa 1500
```

<210> SEQ ID NO 4
<211> LENGTH: 1500
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 4

```
tcagtttcac ggttatgtga gctgtctccg cgtgaggcag taacctctgt gtcatggata 60
caggctggta cacatttggc agtaggaaca caatctggtt tagttgaaat atgggacgcc 120
acgacgtcca aatgtacaag atcaatgact gggcattcgg cccgaacctc agcgctgagt 180
tggaaccgtc atgttttgag ttctggttca agagatcgca gtatcttaca tcgggatgta 240
cgtgcagcag ctcactatac aagtcgcatt gttgaacacc gccaagaggt ttgtggctta 300
cgttggaacg tggatgaaaa caagctggcc agtggttcca atgataaccg tatgatggta 360
tgggatgcac tgcgtgtaga acagcccctt atgaaagttg aagagcatac tgcggctgtt 420
```

```
aaggcgttgg catggtcacc tcatcaacgt ggaatactgg cttcgggtgg aggtactgct 480
gacagacgta tcaaggtgtg gaatacttta acaggatcca agctgcacga tgttgatact 540
ggatctcaag tttgtaatct cttgtggtct cgcaattcta atgaattggt aagtactcat 600
ggatattctc gaaaccaagt cgttatttgg aaatatccgc aaatgaagca actagcatct 660
ttgactggtc atacttatcg agtcctttac ctttccatgt cacctgatgg aactacagtc 720
gtaacggggg ctggagacga aactttaaga ttttggaact gtttcgagaa gtcacgacaa 780
agcggaggag gatcaatatt actagacgct tttagtcagc ttcgttaaat taccaccaaa 840
tttggtgcaa aagggcccat atggtgctac aaccaaagga actttctaat tttgataatg 900
atgtcatttc tctcatcggg atgaaaatag aagtcgaaag gatttttgtc actatttcaa 960
gccccacctg cagctggcag catttctatt gtttatgcat tgtcatttat gggaaaacta 1020
agaaagttcc tctccacccg gactccactg gtaaatatgc gatatcggaa tcatgaccaa 1080
cccatatttt gatcctaatc atttcggttc tagtctccga tcggactccg taaaactgcg 1140
gagtgaactc caacggagaa tactgcagcc aatctcatat ttcatttgtt atttgtccct 1200
caactgtctc gataaggtca tctgtgtttg actagatgtt cgtcattggc atgtcaaaca 1260
aggctagacc ttacaatcat ctcttacgaa tgtaagtgaa tgtaactata ttttccttgc 1320
tactttaacg aggttaacca accccgcac atccccacac caccgctctt gataagcatc 1380
tccgaaaatg catgacgcga caacttcaag catgttgtat ttactgagtt ttcagcctca 1440
ctatcgatac ctctataaat agaggcactt tcgtctcttc tccctcccca caagaaacca 1500
```

<210> SEQ ID NO 5
<211> LENGTH: 1500
<212> TYPE: DNA
<213> ORGANISM: Artificial Sequence
<220> FEATURE:
<223> OTHER INFORMATION: Description of Artificial Sequence: Synthetic
Oligonucleotide

<400> SEQUENCE: 5

```
agaagtactg ttatgaatcg atcgacgtga catgttgttg atggttctga cttcttgatg      60
tccgcgtttt ctgtctctca atagtggtgt tcggggggaag tatggttcta atacttaaca    120
ggtaagatgg ttgcaatgag cacctggtaa agcaacttga atttcctgcc ctgtctccgt    180
taagttatat tcgactcaag gtccttgctt cctgtctgtt ctgtaaaact tcccctttggt   240
gtcttctata tcaactttaa aaacaaggta gtgtgtcgag cgatagtact gtgtcttttt   300
ccctatgaaa aaaatcgcac catccaagac ttctcacctt caacagcttc aacatcatgt   360
tcggtccttt tagagctacg ctggtcgatc taggaggtct gctatggaaa cgtccttgga   420
gaatgtccaa accacagaaa tatagactcc gcaaaagaat gcaacttgta gactccaata   480
tcgacattat ttaccaggga ctgactgagg agggtctgtc ttgcaaagtg atagataact   540
tgaaacaaaa cttcccaaag gagcatgaag tgctccccaa aaacaagtat accgtgttta   600
acaagacagc caaaaactat agaaagggtg ttcatttggt tccaaaatgg accaagaagt   660
ctttgagaga gaaccccgag ttcttctaat tgcacatttc ttcctgttca tagattatcc   720
cacacatagt tgctcacaaa aaaatcacta tcattttcct ccaccggcag tatatcacta   780
acaccttttat ctttattgta gattataatc tgatcttttat ccttagatgt atctatcatc   840
aaccccatgc tcttgaaaag cttgagtctt aacactgtcg aatcgtagtt ttcttgtaga   900
tcattcgata tcactgcttt ttcttgctct tctaattcgt tgagattctg ggtcaaacta   960
gagattgaat tctgaaggtg attcatgttc atctccagat ctgttattga ttttgctaat  1020
ttaaattttt cgtgttcaag ctcttcgata ctctttaggg tctgttgacg gtcttctgtt  1080
tccaataatt gcttgttgaa ctctttaagt tcgtctctct gtttactgat acgtgacaac  1140
aaatctagct ggtgatcgag tttaagtttc cgtttggagc tcaacagaga aagattttca  1200
ttaatttggt tgatagtttg cacgtccggt tcgatctgaa aattctctat agtcgacctg  1260
attaaggaca cagtctcttg aagatcggac attggattta tggagaaggg agatcaaagc  1320
ggaaccagtt gcactgtttta ccttttccagt cgagatactt atcccacagg gccctcactt  1380
tccaggcaga agtcacctag gaggcgcatc cctccgtttg cttccctcgc gacaaactcc  1440
cctgtaaaag aaaacttcac tgaatcgtac acctaatcat acgacactaa cacagatata  1500
```

<210> SEQ ID NO 6
<211> LENGTH: 1500
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 6

```
gtcctttcca aattttttggt tgaaggcatc gcttaaatta tgagcaggat cggtggaaat      60
aagcaggtat ttcttgttag gattgtgaag ggcaagctgg atagatatag aagaagatgt    120
cgtggttta ccgacacccc ccttacctcc aacaaagatc cacttcagcg attcgtggtt    180
cacaattgat cgcaaacttg gctctgcctc aatatccatg gttgatgtct agttgagtgg    240
cgtttgtggt ctcttgatga gttcaaggcg aaagaatatg ataggaaagc atggtttgaa    300
cttttcgcga aagaaggaat actgttccgc gagaaactcc ccggtgccag aaccttccat    360
tgaggttaat cggtgggagg tgttcgaatg acaatgtcag acaaggcgaa cacgtcttgt    420
gacaccagct ggactaagaa gattcggtat gcaccgaaga agaaggccgt gtctcaattg    480
```

| | | | |
|---|---|---|---|
| gcaactttgc | aacaaactac | ggaggaaaag | tctcacaagc | ttttaaccaa | gttgaatcac | 540 |
| gacgacaacg | ataaagaaat | cctcaaccat | ctaacacatg | aagtacaaag | tagaaatgtg | 600 |
| atcttattgg | acaaactaga | ggagctcaac | aaggaactgg | gctggattaa | agaccgaaaa | 660 |
| tgaggaacca | tgagcactgg | gcgttttccag | aaaaactgca | accaacgatg | ggaaaatgat | 720 |
| accacactac | tatggtcacc | ccacattgtg | aaatttcaaa | ccaaaaaaga | tcaaccccat | 780 |
| aattccccag | agggttttcc | caacaatttt | ccaacggact | tgataatgag | tcagatcatt | 840 |
| tgagcatatt | catcttaccc | cttattccgt | gacaatttac | ctattccatt | caaagcatac | 900 |
| ggtatcccgt | gaccttctca | tggagatcat | tctccaccga | tacagcatat | acacagatat | 960 |
| acccaactaa | tatcaattgg | accttgatat | ggtcgacctt | gatggtcccg | tccaacctta | 1020 |
| aaacttagtt | taatgctata | ctttcgcctt | gaaccaaatc | tgtctccccc | tcaatcatct | 1080 |
| ctatgcaaga | aggtcaacac | tgattacgtg | agcaacagcc | agcaatcgtt | cgagtccccg | 1140 |
| ccaaaaaagg | cggagttact | gctccttgtg | accacacccc | ctgagaccac | gtccctaaac | 1200 |
| gatccttgtc | ggttccttcg | tccaattggc | aattgccacg | catacgtgaa | tcgttattgt | 1260 |
| ttcgcctacc | ttgcgtcatt | cgttccagaa | tgttcgacat | actcctctag | aacataccgt | 1320 |
| cacaccacca | tcttaagtta | tcttcacgtg | accatgacgt | acattgtagt | tgactacccc | 1380 |
| attctcatca | ttccgatgcg | gccaaaaatc | tctatataaa | gaccgtatcc | cctaatattc | 1440 |
| tcttcttgtt | aagacattaa | cttagttaat | tcaccaatta | tcacttata | aacaaacaaa | 1500 |

<210> SEQ ID NO 7
<211> LENGTH: 1500
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 7

| | | | |
|---|---|---|---|
| gtttctcttg | gggagatact | ttttcgcgt | gctcctccgt | gcggaacttc | cttctgagct | 60 |
| tctacctctc | agattagtct | aatcgcatca | ggaataagac | tgagaatgct | tttaaggaga | 120 |
| ggcttgagat | tggctaattg | cgttccgaag | tactctttca | aaaggagtta | tacccctctc | 180 |
| aactacgatt | ctctaaagaa | ttatcgtagg | catgctcagg | cgcctcaacc | ccatcagttt | 240 |
| gacgccacta | gatgggacca | acaaccagtt | actaatgagc | aaggagtaat | actcccatcc | 300 |
| gactcaattg | caaacattct | gagacaacca | actctggtca | tagaacggca | aatggaaatg | 360 |
| atgaatatat | ttttaggatt | tgagcaggcg | aaccgatatg | ttatcatgga | tcctacagga | 420 |
| agtattttgg | gttacatgct | agaaagggat | ctgggcatca | ccaaagctat | attgagacag | 480 |
| atctaccgtt | tgcatcgacc | ttttacagtg | gatgtaatgg | atactgcagg | aaatgtatta | 540 |
| atgacaatca | agaggccgtt | tagtttcatc | aattcgcaca | tcaaagctat | attccccct | 600 |
| ttcaggaaca | gcgacccaga | cgaacatgta | attggagaat | ccgttcaaag | ctggcatcct | 660 |
| tggagacgaa | gatacaatct | atttacagca | caaattggcg | aaaaggacac | tgtctacgat | 720 |
| cagttcgggc | acattgacgc | accgtttctt | tcctttgagt | ttcctgtact | ttcagaatct | 780 |
| aggcaaacgc | taggtgctgt | ctctagaaac | ttcgtgggct | ttgcaagaga | gcttttcaca | 840 |
| gatacaggag | tttacatcat | ccgtatgggg | cctgaatctt | ttgtagggct | agaagggaac | 900 |
| tacgggaaca | atgtggccca | acatgccctt | acgctggacc | aaagggctgt | attattagcc | 960 |
| aatgccgttt | caattgactt | tgattacttt | tctaggcact | cgtcacacag | tggtggcttc | 1020 |

-continued

```
attgggtttg aggaatagac agggtctcgt caactcagct cctgccacca aaccaatcat    1080
tgatcaacga gcacactttt gtccacgtga gatcgcttt gcttgcagaa agagcaatgc     1140
atgaaaacgg caaacgcaaa acgagcaaaa aaacgagtaa ataactacaa tttcaccacc    1200
aacagggtca aagagctttt gagacactat aaaaggggcc ctttcccccc aggttccttg    1260
aaatcctcat tcaattatgt tttttactca taatttgact caattggcat cttcttcttt    1320
gttcatatac agtaattgat atgacgctta gtcattatta gtgttctcga ctagcagtgg    1380
cgaaaaaagg gggagttatt ttctagaacc gaccgcaaac tataaaagaa agctgcccct    1440
catataccct tcgaattctt tattttctgt gtttcttccc tatttaacat ctacacaaaa    1500
```

PROMOTER FOR YEAST

CROSS-REFERENCE TO RELATED APPLICATIONS

The present application claims the benefit of priority to U.S. Application No. 62/682,053, filed on Jun. 7, 2018, the contents of which are incorporated herein in their entirety.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

SEQUENCE LISTING

This application includes a nucleotide and amino acid sequence listing in computer readable form (CRF) as an ASC II text (.txt) file according to "Standard for the Presentation of Nucleotide and Amino Acid Sequence Listings in International Patent Applications Under the Patent Cooperation Treaty (PCT)" ST.25. The sequence listing is identified below and is hereby incorporated by reference into the specification of this application in its entirety and for all purposes.

| File Name | Date of Creation | Size (bytes) |
| --- | --- | --- |
| 170840_ST25.txt | Jun. 6, 2018 | 14.8 KB (15,177 bytes) |

BACKGROUND

Field

Despite numerous disadvantages to using methanol in protein expression, methanol inducible promoters, such as the AOX1 promoter ($P_{AOX1}$), have been widely used in Komagataella yeast expression systems for protein expression. As described herein, a promoter that can drive protein expression independently of methanol has been identified that works well with a variety of proteins for expression, such as enzymes.

Description of the Related Art

Komagataella phaffii is a successful system for the production of a wide variety of recombinant proteins that are not native to the Komagataella cell. Several factors have contributed to its success as a protein manufacturing system, some of which include: (1) a promoter derived from the alcohol oxidase I (AOX1) gene of K. phaffii that is well suited for controlled expression of foreign genes; (2) similarity of techniques needed for the molecular genetic manipulation of K. phaffii to those of S. cerevisiae, which are well established; (3) the strong preference of K. phaffii for respiratory growth, which is a key physiological trait that facilitates its culturing at high-cell densities relative to fermentative yeasts; and (4) the knowledge base on the Komagataella system as described in numerous recent publications. Furthermore, the genome of several K. phaffii species have been sequenced, which allows facilitated studies of the RNA and protein expression pathways. The culturing condition of K. phaffii is also relatively easy, as the cells can grow in a high density culture with high levels of proteins being expressed at the intra- and extra-cellular level.

K. phaffii is a single-celled microorganism that is easy to manipulate and culture. K. phaffii is a eukaryote capable of many of the post-translational modifications performed by higher eukaryotic cells such as proteolytic processing, folding, disulfide bond formation and glycosylation. Thus, the system may help to avoid loss of proteins that may end up as inactive inclusion bodies in bacterial systems, as bacterial systems lack methods of post-translation modifications. Foreign proteins requiring post-translational modification may be produced as biologically active molecules in K. phaffii. Additionally, the K. phaffii system has been shown to give higher expression levels of protein than many bacterial systems.

The ability of K. phaffii to utilize methanol as a sole source of carbon and energy was discovered in the 1970s. There are two alcohol oxidase genes AOX1 and AOX2 which have strongly inducible promoters, the AOX promoters. These genes allow Komagataella to use methanol as a carbon and energy source. For example, the AOX1 protein is produced in response to depletion of some carbon sources, such as glucose, and the presence of methanol. In some cases, the gene encoding a desired heterologous protein can be introduced under the control of the AOX1 promoter, which means that gene expression and subsequent protein expression may be induced by the addition of methanol. As methanol could be synthesized from natural gas, methane, there was an interest in using these organisms for generating yeast biomass or single cell protein (SCP) to be marketed primarily as a high protein animal feed. During the 1970s, media and methods for growing K. phaffii on methanol in continuous culture at high cell densities (<130 g/l dry cell weight) were developed. However, during this same period, the cost of methane increased dramatically due to the oil crisis. Thus, the SCP process was never economically competitive for protein production.

Methods were then developed in the 1980's to produce K. phaffii as a heterologous gene expression system. The AOX1 gene (and its promoter) was isolated and vectors, strains and methods for molecular genetic manipulation of K. phaffii were developed. The combination of strong regulated expression under control of the AOX1 promoter along with the fermentation media and methods developed for the SCP process resulted in high levels of foreign proteins in K. phaffii.

Recombinant protein expression in K. phaffii may be driven by the promoter AOX1 and induced by methanol and repressed by other carbon sources such as glucose, glycerol and ethanol. This induction and repression feature functions as a switch which turns recombinant protein expression on and off under different culture conditions. This switch is advantageous when expressing proteins that are toxic towards the host cell and towards cell growth. However, there are several limitations with this system. As the AOX1 system requires methanol, the toxic and flammable material may require special handling and protocols. Additionally, hydrogen peroxide ($H_2O_2$) may be produced from methanol metabolism, which may also result in the degradation of recombinant proteins by the produced free radicals. The nature of methanol induction also limits where the manufacture location may be, and in some circumstances, may require long fermentation times and high biomass production. The production cost is considered to be high for a traditional *Komagataella* system (methanol inducible system).

As such, promoters that drive protein expression independently of methanol that work as well as or better than methanol inducible promoters, are sought. A promoter that may drive protein expression independently of methanol in yeast may reduce the protein expression cost and fermentation time. Additionally, there would be no need for food grade methanol in the process, thus allowing an easy and robust fermentation method for products such as edible and medical products. Thus, a promoter system for production of protein without the presence of methanol, or a constitutive promoter system would be advantageous for the expression of recombinant proteins in the *K. phaffii* system.

SUMMARY

In a first aspect, a promoter comprising a nucleic acid sequence having at least of 55%, 60%, 65%, 70%, 75%, 80%, 85%, 90%, 99% or more sequence identity to any one of SEQ ID NO: 1-7, or a fragment thereof, wherein the promoter is operably linked to a gene encoding a protein, and the promoter drives the expression of the protein from a yeast cell in absence of methanol, is provided. In some embodiments, the sequence identity is over a region of at least 50, 75, 100, 150, 200, 250, 300, 350, 400, 450, 500, 550, 600, 650, 700, 750, 800, 850, 900, 950, 1000, 2050, 1100, 1150, or more residues, or the full length of the nucleic acid. In some embodiments, the fragment of Seq. ID No: 1-7 is over a region of at least 50, 75, 100, 150, 200, 250, 300, 350, 400, 450, 500, 550, 600, 650, 700, 750, 800, 850, 900, 950, 1000, 2050, 1100, 1150, or more residues, or the full length of the nucleic acid. In some embodiments, the protein is an enzyme, a peptide, an antibody, or a recombinant protein. In some embodiments, the enzyme is a lipase, amylase, xylanase, protease, glucoamylase, glucanase, mannanase, phytase, or cellulase. In some embodiments, the protein is glycosylated. In some embodiments, the protein comprises disulfide bonds. In some embodiments, the nucleic acid sequence is 50, 100, 200, 300, 400, 500, 600, 700, 800, 900, 1000, 1500, 2000, 3000, 4000 or 5000 bases upstream from a translational start site of the at least one sequence encoding the protein or any number of bases in between a range defined by any two aforementioned values upstream from the start site of the at least one sequence encoding the protein. In some embodiments, the yeast cell is a species of methylotrophic yeast. In some embodiments, the yeast cell is of the genus *Komagataella*. In some embodiments, the yeast cell is selected from: *K. farinosa, K. anomala, K. heedii, K. guilliermondii, K. kluyveri, K. membranifaciens, K. norvegensis, K. ohmeri, K. pastoris, K. phaffii, K. methanolica* and *K. subpelliclosa*. In some embodiments, the expression of protein is up to 40 g/l.

In a second aspect, a vector comprising the promoter of any one of the embodiments herein is provided. In some embodiments, the vector is a yeast integrative plasmid, episomal plasmid, centromere plasmid or artificial chromosome. In some embodiments, the vector comprises a selectable marker.

In a third aspect, a yeast cell comprising the promoter or the vector of any one of the embodiments herein is provided.

In a fourth aspect, a protein expression system comprising the yeast cell of any one of the embodiments herein is provided.

In a fifth aspect, a method of expressing protein in a yeast cell is provided. The method comprises providing a yeast cell, introducing the promoter or the vector of any one of any one of the embodiments herein into the cell, fermenting the yeast cell under at least one fermentation condition in the absence of methanol in a nutrient broth, harvesting the cells and recovering protein from the cells. In some embodiments, the protein is excreted or is intracellular. In some embodiments, the protein is an enzyme, a peptide, an antibody, or a recombinant protein. In some embodiments, the enzyme is lipase, amylase, xylanase, protease, glucosamylase, glucanase, mannanase, phytase, or cellulase. In some embodiments, the method further comprises driving protein expression. In some embodiments, the yeast cells are a species of methylotrophic yeast. In some embodiments, the yeast cells are of the genus *Komagataella*. In some embodiments, the yeast cells are selected from the group consisting of *K. farinosa, K. anomala, K. heedii, K. guilliermondii, K. kluyveri, K. membranifaciens, K. norvegensis, K. ohmeri, K. pastoris, K. methanolic, K. phaffii* and *K. subpelliclosa*. In some embodiments, the yeast cell is *K. phafii*. In some embodiments, the nutrient broth comprises at least one carbon source. In some embodiments, the at least one carbon source is selected from a group consisting of dextrose, maltose, glucose, dextrin, glycerol, sorbitol, mannitol, lactic acid, acetate, xylose, or other partially hydrolyzed starches, and any mixtures thereof. In some embodiments, the concentrations of the at least one carbon source varies from 0.0 g/l, 0.5 g/L, 1 g/L, 2 g/L, 4 g/L, 6 g/L, 8 g/L, 10 g/L, 11 g/L, 12 g/L, 13 g/L, 14 g/L, 15 g/L, 16 g/L, 18 g/L, 20 g/L, 22 g/L, 24 g/L, 26 g/L, 28 g/L, 30 g/L, 35 g/L, 40 g/L, 45 g/L, 50 g/L, 55 g/L, or 60 g/L any concentration within a range defined by any two aforementioned values. In some embodiments, the method further comprises addition of the at least one carbon source by pulse or continuous feeding.

DETAILED DESCRIPTION

Figure 1:
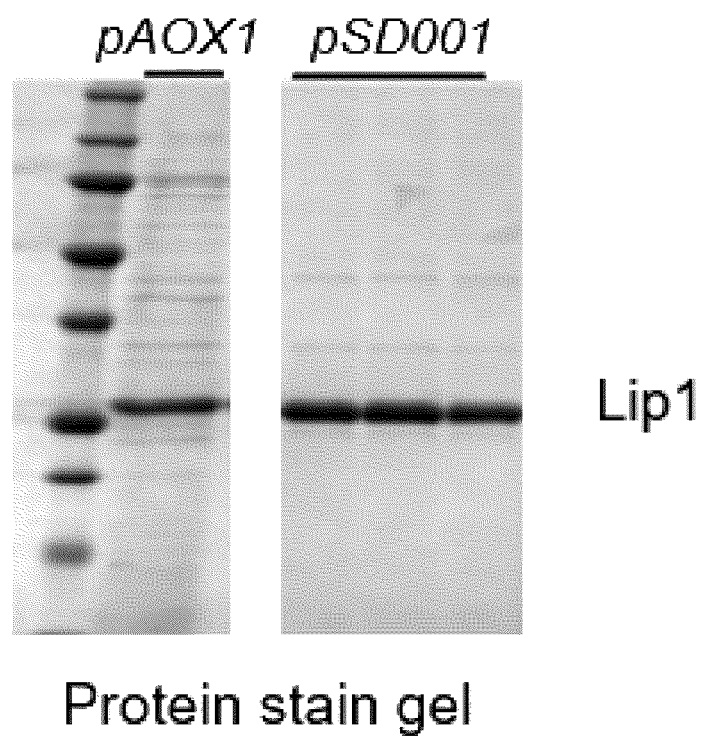
FIG. 1 demonstrates the expression of lipase under the control of the promoter pAOX1 or pSD001 in microtiter plates. Shown are protein PAGE gels in which expression of the lipase is shown under the control of pAOX1 or pSD001.

In the description that follows, the terms should be given their plain and ordinary meaning when read in light of the specification. One of skill in the art would understand the terms as used in view of the whole specification.

As used herein, "a" or "an" may mean one or more than one.

"About" as used herein when referring to a measurable value is meant to encompass variations of ±20% or ±10%, more preferably ±5%, even more preferably ±1%, and still more preferably ±0.1% from the specified value.

"Methylotrophic yeast," as described herein, have its plain and ordinary meaning when read in light of the specification, and may include but is not limited to, for example, a limited number of yeast species that can use reduced one-carbon compounds such as methanol or methane, and multi-carbon compounds that contain no carbon bonds, such as dimethyl ether and dimethylamine. For example, these species can use methanol as the sole carbon and energy source for cell growth. Without being limiting, methylotrophs may include the Genus Methanoscacina, *Methylococcus capsulatus, Hansenula polymorpha, Candida boidinii, Komagataella pastoris* and *Komagataella phaffii*, for example. In the embodiments described herein, a promoter that drive protein expression independently of methanol is provided for protein expression in a methylotrophic yeast cell.

"*Komagataella phaffii*," has its plain and ordinary meaning when read in light of the specification, and may include but is not limited to, for example, a species of methylotrophic yeast. "*Pichia phaffii*" may also refer to the colloquial name as it has officially been renamed *Komagataella phaffii* (for the GS115 strain used herein) or it may be also referred to as *Komagataella pastoris*, depending on which lineage it has.

*Komagataella* is widely used for protein expression using recombinant DNA techniques since its alcohol oxidase promoters were isolated and cloned. Hence it is used in biochemical and genetic research in academia and the biotechnical industry as it can express a wide range of diverse genes as compared to other microorganism such as *Pseudomonas, Bacillus*, and *Aspergillus*. Furthermore, the protein product is easier to purify and leads to a clean product. *Komagataella* is well suited for protein expression as it has a high growth rate and is able to grow on a simple, inexpensive medium. *K. phaffii* can grow in either shaker flasks or a fermenter, which makes it suitable for both small and large scale expression. *K. phaffii* has two alcohol oxidase genes AOX1 and AOX2, which have strongly inducible promoters. These genes allow *Komagataella* to use methanol as a carbon and energy source. The AOX promoters are induced by methanol and are repressed by glucose, for example. Often, the gene for a desired heterologous protein is introduced under the control of the AOX1 promoter, which means that protein expression can be induced by the addition of methanol. In a popular expression vector, the desired protein is produced as a fusion product to the secretion signal of the α-mating factor from *Saccharomyces cerevisiae* (baker's yeast). This causes the protein to be secreted into the growth medium, which greatly facilitates subsequent protein purification. *Komagataella* also has advantages over *S. cerevisiae* as well. *Komagataella* can easily be grown in cell suspension in reasonably strong methanol solutions that would kill most other micro-organisms, a system that is difficult to set up and maintain. As the protein yield from expression in a microbe is roughly equal to the product of the protein produced per cell and the number of cells, this makes *Komagataella* of great use when trying to produce large quantities of protein without expensive equipment. However, *Komagataella* may be unable to produce proteins for which the host may lack the proper chaperones. As such, *Komagataella* may be co-transformed with a nucleic acid or a gene that encodes a chaperone for proper protein folding.

"Chaperone protein," "molecular chaperones," or "chaperones" have their plain and ordinary meaning when read in light of the specification, and may include but is not limited to, for example, proteins that assist the covalent folding or unfolding and the assembly or disassembly of other macromolecular structures. Chaperones are present when the macromolecules perform their normal biological functions and have correctly completed the processes of folding and/or assembly. The chaperones are concerned primarily with protein folding. In some embodiments of the promoter, the promoter may drive protein expression independently of methanol. The protein may be a recombinant protein, such as for example, an enzyme. In some embodiments, a chaperone is expressed with the enzyme, wherein the chaperone assists in the folding of the enzyme. In some embodiments, expression of a chaperone leads to a functional enzyme. In some embodiments, the chaperone is expressed with a recombinant protein. In some embodiments, the promotor produces constitutively and is independent on the presence of methanol.

The budding yeast of strain *K. phaffii*, can grow on methanol and has been widely used for over 30 years for heterologous protein expression. For example, over 70 products including therapeutic biologicals (mostly) and industrial enzymes have been produced using the *K. phaffii* system. Protein from the system may be either secreted (>16 g/L) or produced for intracellular expression (>20 g/L). Most enzyme companies produce enzymes using a native host or homologous expression of the enzyme. However no native enzymes from *Komagataella* have been discovered for industrial use. Also appreciated by those skilled in the art, are methods for genome sequencing and molecular tools available for strain manipulation. Growth of the cells, fermentation and expression process are also well developed as the system has a long history of safe use and is regulatory friendly. Methods of growth of a typical culture for protein expression can be appreciated by those of skill in the art. In the embodiments provided herein, *K. phaffii* is used as an expression host for the expression of protein in a methanol-free environment.

"Nucleic acid" or "nucleic acid molecule" have their plain and ordinary meaning when read in light of the specification, and may include but is not limited to, for example, polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. Nucleic acids can be either single stranded or double stranded. In some embodiments, a nucleic acid sequence encoding a fusion protein or recombinant protein is provided, wherein the protein expression is driven by a promoter that drives protein expression independent of methanol. In some embodiments, the nucleic acid comprises a promoter that is not inducible by methanol. In some embodiments, a cell comprising the nucleotide for protein expression that is independent of methanol is provided.

"Coding for" or "encoding" are used herein, and have their plain and ordinary meaning when read in light of the specification, and may include but is not limited to, for example, the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system. In some embodiments, a vector comprises a nucleic acid encoding a protein, wherein the nucleic acid encoding the protein is under the influence of a promoter that drives protein expression independently of methanol.

A "nucleic acid sequence coding for a polypeptide" has its plain and ordinary meaning when read in light of the specification, and may include but is not limited to, for example, all nucleotide sequences that are degenerate versions of each other and that code for the same amino acid sequence.

"Vector," "expression vector" or "construct" have their plain and ordinary meaning when read in light of the specification, and may include but is not limited to, for example, a nucleic acid used to introduce heterologous nucleic acids into a cell that has regulatory elements to provide expression of the heterologous nucleic acids in the cell. The vector, as described herein, is a nucleic acid molecule encoding a gene that is expressed in a host-cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter. Vectors include but are not limited to plasmid, minicircles, yeast, and viral genomes. Available commercial vectors are known to those of skill in the art. Commercial vectors are available from European Molecular Biology Laboratory and Atum, for example.

A "promoter that drives protein expression independently of methanol," has its plain and ordinary meaning when read in light of the specification, and may include but is not limited to, for example, a promoter that may allow an increase in the expression of a specific gene in the absence of methanol.

"Constitutive promoter," has its plain and ordinary meaning when read in light of the specification, and may include but is not limited to, for example, a promoter that is active in most circumstances in the cell. In some embodiments, the promoter drives heterologous protein expression independent of methanol, in yeast. In some embodiments, the yeast cells are a species of methylotrophic yeast. In some embodiments, the yeast cells are of the genus *Komagataella*. In some embodiments, the promoter is a constitutive promoter that may drives expression in the absence of methanol.

"Protein expression," "protein expression," have their plain and ordinary meaning when read in light of the specification, and may include but is not limited to, for example, the biotechnological process of generating a specific protein. It may be achieved by the manipulation of gene expression in an organism such that it expresses large amounts of a recombinant gene. Without being limiting, this may include the transcription of the recombinant DNA to messenger RNA (mRNA), the translation of mRNA into polypeptide chains, which are ultimately folded into functional proteins and may be targeted to specific subcellular or extracellular locations.

"Fusion proteins" or "chimeric proteins" have their plain and ordinary meaning when read in light of the specification, and may include but is not limited to, for example, proteins created through the joining of two or more genes that originally coded for separate proteins or portions of proteins. The fusion proteins can also be made up of specific protein domains from two or more separate proteins. Translation of this fusion gene can result in a single or multiple polypeptides with functional properties derived from each of the original proteins. Recombinant fusion proteins can be created artificially by recombinant DNA technology for use in biological research or therapeutics. Such methods for creating fusion proteins are known to those skilled in the art. Some fusion proteins combine whole peptides and therefore can contain all domains, especially functional domains, of the original proteins. However, other fusion proteins, especially those that are non-naturally occurring, combine only portions of coding sequences and therefore do not maintain the original functions of the parental genes that formed them. In some embodiments, promoters are provided that drive protein expression independently of methanol and are useful in driving protein expression in yeast. In some embodiments, the promoter is useful in driving expression of a fusion protein.

"Promoter" has its plain and ordinary meaning when read in light of the specification, and may include but is not limited to, for example, a nucleotide sequence that directs the transcription of a structural gene. In some embodiments, a promoter is located in the 5' non-coding region of a gene, proximal to the transcriptional start site of a structural gene. Sequence elements within promoters that function in the initiation of transcription may also be characterized by consensus nucleotide sequences. These promoter elements include RNA polymerase binding sites, TATA sequences, CAAT sequences, differentiation-specific elements (DSEs; McGehee et al., Mol. Endocrinol. 7:551 (1993); incorporated by reference in its entirety), cyclic AMP response elements (CREs), serum response elements (SREs; Treisman, Seminars in Cancer Biol. 1:47 (1990); incorporated by reference in its entirety), glucocorticoid response elements (GREs), and binding sites for other transcription factors, such as CRE/ATF (O'Reilly et al., J. Biol. Chem. 267:19938 (1992); incorporated by reference in its entirety), AP2 (Ye et al., J. Biol. Chem. 269:25728 (1994); incorporated by reference in its entirety), SP1, cAMP response element binding protein (CREB; Loeken, Gene Expr. 3:253 (1993); incorporated by reference in its entirety) and octamer factors (see, in general, Watson et al., eds., Molecular Biology of the Gene, 4th ed. (The Benjamin/Cummings Publishing Company, Inc. 1987; incorporated by reference in its entirety)), and Lemaigre and Rousseau, Biochem. J. 303:1 (1994); incorporated by reference in its entirety). A promoter may be constitutively active, repressible or inducible. If a promoter is an inducible promoter, then the rate of transcription initiation increases in response to an inducing agent. In contrast, the rate of transcription initiation is not regulated by an inducing agent if the promoter is a constitutive promoter. Repressible promoters are also known. In some embodiments, a gene delivery polynucleotide or vector is provided. In some embodiments, the gene delivery polynucleotide comprises a promoter sequence. The promoter can be specific for bacterial, mammalian or yeast expression, for example. In some embodiments, wherein a nucleic acid encoding a protein of interest is provided, the nucleic acid further comprises a promoter sequence. In some embodiments, the promoter is specific for expression in yeast. In some embodiments, the promoter is a conditional, inducible or a constitutive promoter. In some embodiments, the promoter is a promoter that is useful in driving protein expression independently of methanol, wherein the promoter drives protein expression in a methanol-free media. The promoters isolated herein may be inducible or constitutive and may drive protein expression in the absence of methanol.

"Conditional" or "inducible" have their plain and ordinary meaning when read in light of the specification, and may include but is not limited to, for example, a nucleic acid construct that includes a promoter that provides for gene expression in the presence of an inducer and does not substantially provide for gene expression in the absence of the inducer. In some embodiments, the promoter is an inducible promoter. In some embodiments, the promoter is an inducible promoter for yeast protein expression.

"Regulatory element" has its plain and ordinary meaning when read in light of the specification, and may include but is not limited to, for example, a regulatory sequence, which is any DNA sequence that is responsible for the regulation of gene expression, such as promoters and operators. The regulatory element can be a segment of a nucleic acid molecule, which is capable of increasing or decreasing the expression of specific genes within an organism. In some alternatives described herein, the gene is under a control of a regulatory element.

"Host cell" has its plain and ordinary meaning when read in light of the specification, and may include but is not limited to, for example, a cell that is introduced with a nucleic acid or vector that encodes a protein or gene of interest. In some embodiments, the host cell is an isolated cell. In the embodiments, described herein, the host cell is a yeast cell. In some embodiments, the cell is a methylotroph yeast cell. In some embodiments, the yeast cell is of *Komagataella phaffii*. In some embodiments, promoters that drive protein expression independently of methanol that are useful in driving protein expression in yeast is provided. In some embodiments, the promoter drives heterologous protein expression in yeast. In some embodiments, the yeast cells are of the genus *Komagataella*. In some embodiments, the isolated host cell is a yeast cell. In some embodiments, the isolated host cell is *Komagataella phaffii*.

The term "gene expression" refers to the biosynthesis of a gene product. For example, in the case of a gene encoding a structural protein, gene expression involves transcription of the gene into mRNA and translation of mRNA into the structural protein.

"Protein" has its plain and ordinary meaning when read in light of the specification, and may include but is not limited to, for example, a macromolecule comprising one or more polypeptide chains. A protein can also comprise non-peptide components, such as carbohydrate groups. Carbohydrates and other non-peptide substituents, such as post-translational modifications, can be added to a protein by the cell in which the protein is produced, and will vary with the type of cell. Proteins are defined herein in terms of their amino acid backbone structures; substituents such as carbohydrate groups are generally not specified, but can be present nonetheless. In some embodiments, a gene delivery polynucleotide or vector, is provided for expression protein, in a methanol independent method, in a *Komagataella* system. In some embodiments, the gene delivery polynucleotide or vector further comprises a sequence for at least one protein.

"Gene" has its plain and ordinary meaning when read in light of the specification, and may include but is not limited to, for example, the molecular unit of heredity of a living organism, describing some stretches of deoxyribonucleic acids (DNA) and ribonucleic acids (RNA) that code for a polypeptide or for an RNA chain that has a function in the organism, and can be a locatable region in the genome of an organism.

Genetic modification performed by transformation is described herein. "Transformation" refers to transferring genetic material, such as, for example, nucleic acids, PCR amplified nucleic acids, or synthetic DNA or RNA, to a cell. Common techniques employed for transferring genetic material may use viruses or viral vectors, electroporation, and/or chemical reagents to increase cell permeability. In some alternatives herein, the isolated host cell is transformed by electroporation. In some embodiments, the isolated host cell is transformed by exposure to alkali cations in the presence of a vector, plasmid or DNA.

Various transformation techniques have been developed and can be appreciated by one of skill in the art. Thus, gene transfer and expression methods are numerous but essentially function to introduce and express genetic material in yeast cells "Sequence Identity", "% sequence identity", "% identity", "% identical" or "sequence alignment" means a comparison of a first amino acid sequence to a second amino acid sequence, or a comparison of a first nucleic acid sequence to a second nucleic acid sequence and is calculated as a percentage based on the comparison. The result of this calculation can be described as "percent identical" or "percent ID."

Generally, a sequence alignment can be used to calculate the sequence identity by one of two different approaches. In the first approach, both mismatches at a single position and gaps at a single position are counted as non-identical positions in final sequence identity calculation. In the second approach, mismatches at a single position are counted as non-identical positions in final sequence identity calculation; however, gaps at a single position are not counted (ignored) as non-identical positions in final sequence identity calculation. In other words, in the second approach gaps are ignored in final sequence identity calculation. The difference between these two approaches, i.e. counting gaps as non-identical positions vs ignoring gaps, at a single position can lead to variability in the sequence identity value between two sequences.

A sequence identity is determined by a program, which produces an alignment, and calculates identity counting both mismatches at a single position and gaps at a single position as non-identical positions in final sequence identity calculation. For example program Needle (EMBOS), which has implemented the algorithm of Needleman and Wunsch (Needleman and Wunsch, 1970, J. Mol. Biol. 48: 443-453), and which calculates sequence identity per default settings by first producing an alignment between a first sequence and a second sequence, then counting the number of identical positions over the length of the alignment, then dividing the number of identical residues by the length of an alignment, then multiplying this number by 100 to generate the % sequence identity [% sequence identity=(# of Identical residues/length of alignment)×100)].

A sequence identity can be calculated from a pairwise alignment showing both sequences over the full length, so showing the first sequence and the second sequence in their full length ("Global sequence identity"). For example, program Needle (EMBOSS) produces such alignments; % sequence identity=(# of identical residues/length of alignment)×100)].

A sequence identity can be calculated from a pairwise alignment showing only a local region of the first sequence or the second sequence ("Local Identity"). For example, program Blast (NCBI) produces such alignments; % sequence identity=(# of Identical residues/length of alignment)×100)].

The sequence alignment is preferably generated by using the algorithm of Needleman and Wunsch (J. Mol. Biol. (1979) 48, p. 443-453). Preferably, the program "NEEDLE" (The European Molecular Biology Open Software Suite (EMBOSS)) is used with the programs default parameter (gap open=10.0, gap extend=0.5 and matrix=EBLOSUM62 for proteins and matrix=EDNAFULL for nucleotides). Then, a sequence identity can be calculated from the alignment showing both sequences over the full length, so showing the first sequence and the second sequence in their full length ("Global sequence identity"). For example: % sequence identity=(# of identical residues/length of alignment)×100)].

The variant nucleic acids are described by reference to a nucleic acid sequence which is at least n % identical to the nucleic acid sequence of the respective parent enzyme with "n" being an integer between 80 and 100. The variant nucleic acids include sequences that are at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical when compared to the full-length sequence of the parent nucleic acid according to SEQ ID Nos. 1-7, wherein the variant is a promoter.

The variant nucleic acid comprises at least one modification compared to the parent nucleic acid. The variant nucleic acid of the present invention comprises at least one nucleotide substitution, nucleotide insertion and/or nucleotide deletion compared to the parent nucleic acid.

The yeast *Komagataella phaffii* has been widely used as a heterologous protein expression host. Strong inducible promoters derived from methanol utilization genes or constitutive glycolytic promoters are typically used to drive gene expression. Notably, genes involved in methanol utilization are not only repressed by the presence of glucose, but also by glycerol.

As described herein, novel promoters that drive protein expression independently of methanol to drive high heterologous expression in scale-relevant fermentation conditions in *Komagataella phaffii* are provided. Use of the promoters may lower the overall biomass and reduce cost of the expression of protein. Thus, the promoters described herein, drive protein expression independently of methanol and are helpful for allowing robust and efficient high throughput screening in *Komagataella*.

As described herein, the identified promoters may influence heterologous gene expression using fermentation conditions.

Some promoters for expression of genes in the absence of methanol have been previously described. For example, inducible promoters have previously been published for small molecule induction. Without being limiting, current promoters that induced independently of methanol include SUC2, $P_{CUP1}$, $P_{GAL1}$ $P_{ADH}$, for example. However, the inducers for these specific promoters can be expensive. In addition, carbon-source dependent promoters have also been published. These can rely on relatively expensive carbon sources and can also be repressed by glucose, such as $P_{ADH2}$, GLK1, HXK2 and P1S1, for example. Likewise, constitutive promoters have also been described, such as the glyceraldehyde-3-phosphate dehydrogenase (GAP). (Weinhandl et al. 2014; included by reference in its entirety herein).

A problem with such known systems of promoters that drive protein expression independently of methanol for *Komagataella* is that these promoters have a weaker activity compared to the methanol-inducible AOX1 promoters. Previous studies have focused on strong promoters from shaker flask conditions, which might not correlate well to performance in scale-relevant or full-scale fermentation conditions. An ideal promoter would be strongly induced under scale-relevant fermentation conditions.

Thus, promoters that drive protein expression independently of methanol, are commercially desired to enable robust processes of protein expression, low-cost medium components, and lower levels of biomass.

Described herein are identified *Komagataella* native promoters that are capable of driving protein expression in a media that lacks methanol.

The recombinant expression system driven by methanol induction has several limitations. As the promoter $P_{AOX1}$ requires methanol, the methods require special handling and may not be suitable in the expression of edible and medical products. Additionally, the use of methanol may lead to the by-product hydrogen peroxide ($H_2O_2$) from methanol metabolism which is known to lead to oxidative stress, which may lead to the degradation of the recombinant protein one is wishing to express.

Example 1: Expression of Proteins Under the Control of the Promoters

Expression vectors are constructed with the promoter regions upstream of a gene for expression of a fusion protein or an enzyme, such as lipase. Vectors for protein expression may be constructed with the promoter placed immediately upstream of the translational start site of a gene encoding the protein. Thus, in some embodiments, these vectors can be used for transforming cells for protein expression in the absence of methanol. In some embodiments the cells are *Komagataella* cells.

Protein expression from the *Komagataella* cells may be assayed under fermentation conditions. It should be expected that the promoters described herein will drive protein expression independent of methanol (SEQ ID NO: 1-7).

Example 2 Expression of Proteins Under the Control of a Promoter

Figure 2:
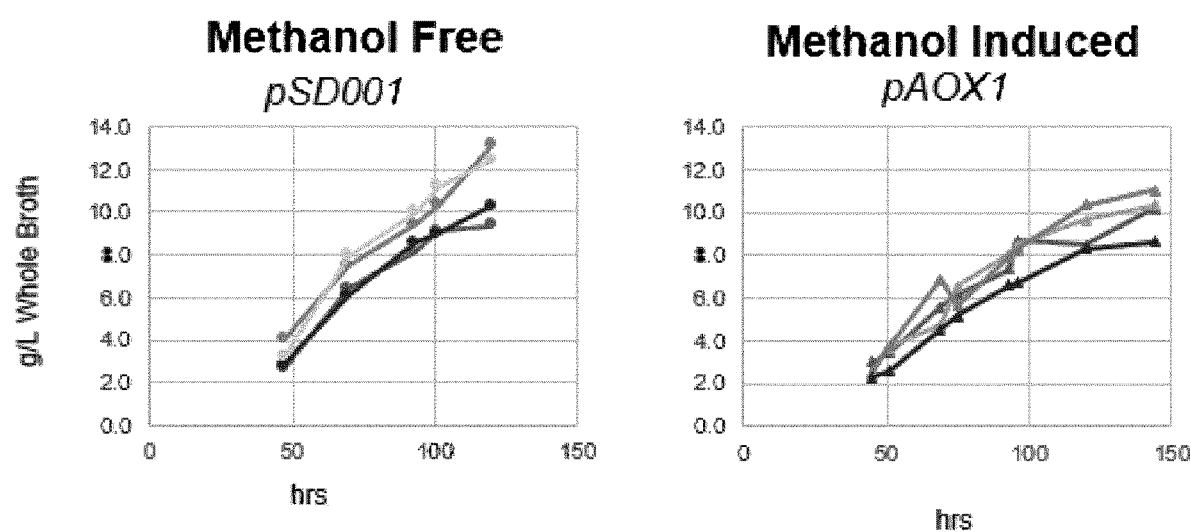
FIG. 2 demonstrates the lipase fermentation yields from 45 to 150 hours in a broth that is deficient in methanol and a broth for methanol induction. As shown, the promoter pSD001 drives more lipase expression in the absence of methanol than the pAOX1 promoter in methanol induction conditions over the same period of time.

As shown in FIG. 1, the isolated promoter, pSD001 when compared to the control pAOX1, was able to drive expression of Lipase 1 in the absence of methanol in microtiter plates. Assays to measure the yield of lipase in fermentation broth were also performed which show that the pSD001 promoter led to expression of the marker protein, Lipase in fermentation broth in the absence of methanol (FIG. 2). In both microtiter plate and fermentation conditions, the expression of lipase 1 was higher in methanol-free conditions using the pSD001 promoter than in methanol induction conditions using the pAOX promoter.

Figure 3:
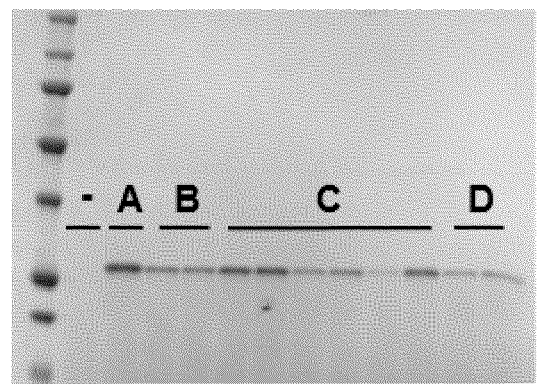
FIG. 3 shows a schematic of the promoter pSD001 as three functional forms, a 1.5 kb promoter, a 1 kb promoter and a 0.66 kb promoter for driving expression of lipase 1 (1.5 kb promoter (A)) and lipase 2 (1.5 kb promoter (B), 1 kb promoter (C) and 0.66 kb promoter (D)). As shown in the protein PAGE gel, all variations of the promoter were able to drive expression of the lipases.

Several variations of the pSD001 promoter were constructed as shown in the diagram on FIG. 3. These constructs were then ligated to Lipase 1 or Lipase 2 genes and placed in an expression vector. As shown, a 1.5 kb promoter, a 1 kb promoter and a 0.66 kb promoter for driving expression of lipase 1 (1.5 kb promoter (A)) and lipase 2 (1.5 kb promoter (B), 1 kb promoter (C) and 0.66 kb promoter (D)) were used to drive lipase expression. As shown in FIG. 3, the protein PAGE gel, all variations of the promoters were able to drive expression of the lipases.

Figure 4A:
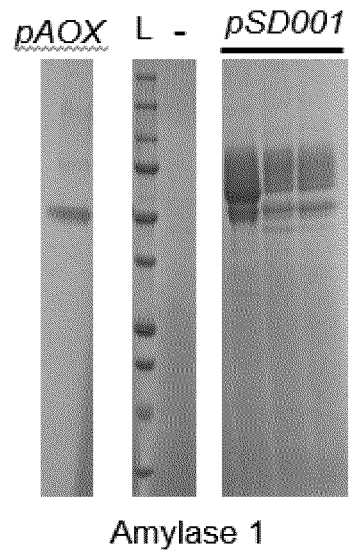
FIGS. 4A, 4B, and 4C are an array of protein gel assays which demonstrate the expression of amylase 1 and 2 and a xylanase under the control of the promoter pSD001 in yeast cells in methanol-free expression conditions.
Figure 4B:
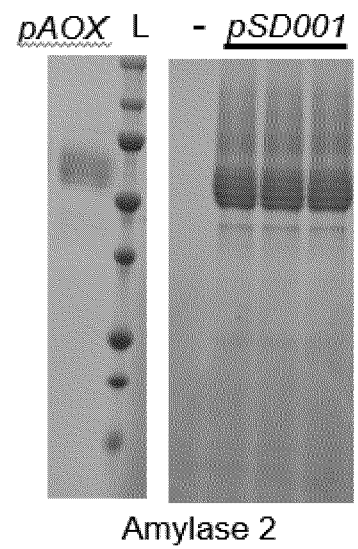
Figure 4C:
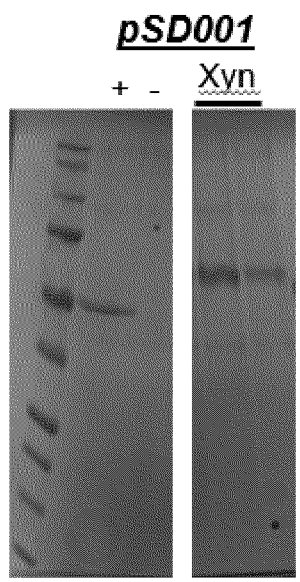

The pSD001 promoter was also tested for driving expression of other classes of enzymes. As shown in the panels, the promoter was able to drive expression of two amylases (amylase 1 and 2) and a xylanase in the absence of methanol. (FIG. 4A-4C).

Figure 5:
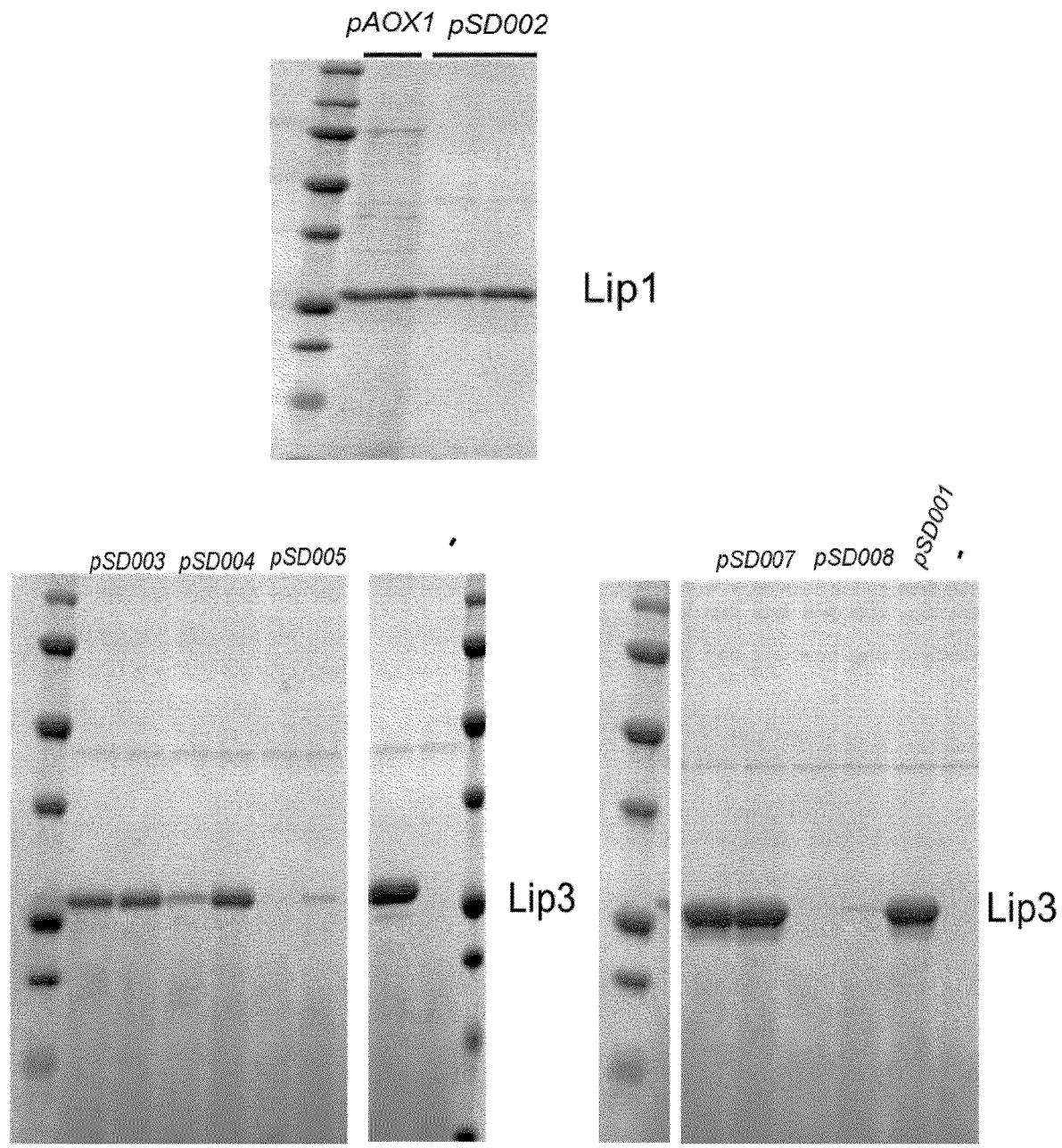
FIG. 5 is a panel of protein gel assays which demonstrate the expression of lipase 1 and 3 under the control of several promoters (pSD001, pSD002, pSD003, pSD004, pSD005, pSD007, pSD008) in yeast cells in methanol-free expression conditions in microtiter plates.
Figure 6:
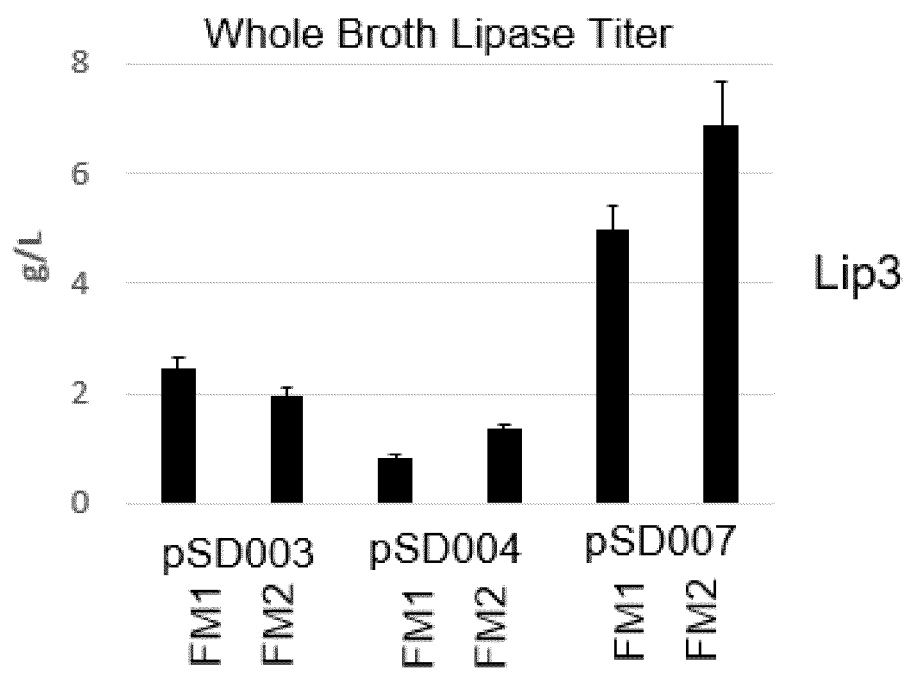
FIG. 6 shows whole broth fermentation yields of lipase 3 expressed in yeast cells under the control of the promoters: pSD003, pSD004 and pSD007. As shown, the pSD007 promoter led to the most expression of lipase between the promoters under two different methanol-free fermentation conditions at 120 hrs.

Various promoters were also tested for the ability to drive protein expression of lipase 1 and lipase 3 (Promoters: pSD001 (SEQ ID NO: 1), pSD002 (SEQ ID NO: 2), pSD003 (SEQ ID NO: 3), pSD004 (SEQ ID NO: 4), pSD005 (SEQ ID NO: 5), pSD007 (SEQ ID NO: 6) and pSD008 (SEQ ID NO: 7)). All promoters can drive lipase expression to various levels in microtiter plates, as shown in FIG. 5. The promoters: pSD003, SD004 and pSD007 were also tested in methanol-free fermentation conditions. As shown in FIG. 6, all three promoters led to lipase expression and the promoter pSD007 led to the most expression of protein.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those of skill within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

Any of the features of an embodiment of any one of the aspects is applicable to all aspects and embodiments identified herein. Moreover, any of the features of an embodiment any one of the aspects is independently combinable, partly or wholly with other embodiments described herein in any way, e.g., one, two, or three or more embodiments may be combinable in whole or in part. Further, any of the features of an embodiment of any one of the aspects may be made optional to other aspects or embodiments.

Sequences

```
pSD001-SEQ ID NO: 1
TCCAGTGTAGCACTAAAATCTAATATCTTCGGCTTTATACTTTTTTGTTC

ATCCGAAAGCTTACGAACAATTCTTTCTCCTGTTTTATTGTGGATATAGA

CAATTTCGTCAGTTTCTTGGAGAGAAGAGTTATTTCCGGTTTTGGCTGGC

CCTATAAACGGGTTCTTGGATTTGGATCTAGTAATAAAAATGTCACTGTC

ATTCTCGGAGCTGAACTTTGTGTTGTACGAAGATGGGTTGTTCCACTGTT

TTGCCAGCTCTTCATTGATGATTTTCTTAGTGGGTGTTCTTGGAGGTTCA

CGTTGCCTATAATCTTGACGTTCTTCTTCATCACTATCGATGCCATCAAA

ATTAAGCGTCCTTATTGCAGGCTTTTGTGATTTCAACTGCAATCCTTCTA

TCTCTTCATCAGAGCTTTCGAACTGAATACTATCACTCAAAACTGGCGAC

ATTGCACATTTCCGCAAACCATTTCGGGAATCTATGCTAGCTCTTCTAGA

CGATAAAGAACGACCGGAACCAATACGGGGTTGTGCAGGTGGGAATAAAT

ATGTTGGTTTGGATTCTTGACGTGAAGAAGGTATTCTAGTCGATGAAGTG

GTTGATAAGGATATGGCGTCACTGAGTTGTTTTCTTTTCCTATGTTGCGG

TGTTGGGTCAGGAGTTAATTGATTCACCTCCATAACTCTGGAATTTCTTG
```

-continued
AATGTGGGGTTTTCAGATGGGCATCTTTCTTGACGGGGTTGTGAGTAACG

GAGGAACCTGGTGTCTTGGGTGTGAACGGTGTTTGAGCCTGTACGCGGTT

ACTTCTGGGCGGAGTACTCGGAGTCATGAGAGCCATTGATTAGAAGGTGA

ATGAGGGAGTCACCACTCTAAGCAAACAAAATGAGGTCGAAGCAAAAAAT

AAAGTAAAGTAGCACTTCTGGCAGGTTAGATCAAAGAGTGACGGGAGATT

TGAAGATGGCTGGTTTTTCCTTAGTCTTGGAAGAGGTTTGTGTGGGTATC

AGCGAATATTCCCCGATTAGGCAAATTAGTTGCATTGAAATTAACACGAC

ATGGTGATTTGTGGTAACAAATATCTATTGGTGGTTGGTGTGTGGGTGTA

ATAGTGGTCGTGTCATGATGATGGTGTTCAGGTGTTGTCATAGATCGGTC

TTCAGTAAGAGAAGGAAGCTTGGTGACGATCACAGCTATGATGTAATAGA

AATTGCTAAGCAATTGTGAGGTGTGATGTATTTTGCAGAGCAATTGTGCG

GTACAACGGGGTGTTATTGTCTTCACAAGGCATTTATTGCGAATTTCGTA

GTTGAAAGAATATTTTAGCACAGGGTGCTTGACCCCTATTGTTGCTCGCT

AAACCATGATTGCTAAATGATGACATAGCAATCACTTTACTAAGATTGCT

ATAAGGACACCTTTCTTAGTATAAATGGACACTCTTTTCCCCTGCTAAAC

TTCTTTTATTTTTCACACTTAAACAGTTACAAAACACAAACACAACTAGA

A pSD002-SEQ ID NO: 2
GTGCTAAAATCTGAGGTTTACAAGCTGTGATGTTCCCCTAAGATCTCAC

AATCGAACAATCGCGAAGCCAATGCAAGTTGTTTAAGGGGAAACGACTC

ACTATTCCTGAAATTAGTATTCAAAACTTGGTCCGGAAGAACAATGAGG

CGGCCGTTAAAATACTCACGTAAACGGTGTCTACAAGCGCATTAAAATC

CGTTTGAATTCAAGCAAAAGCCACCAGAGGCTTATGCTTGGTTATACCC

AGCATTGACCTTTGGTATGAGCATCTGAAAAACAACCAGGTGTTGCAAA

GTTAAACATCCTTCTTTGTTCATATAGAACCCACTATTCATGGTACTCC

CCAATCGAATTTCACATTCTGGTTTTGAAATTACACACCACGTTAGCTT

ATAAGATTTCATATAACTTATTGATATACGGTTTCCATTGTTCGAATAG

TTGAGGTTGTATGTAATTCGATTGAAGGGGCCATTTTTGTTTCCTACTT

TTCCTGGGAGCTTATCCGATGCGCTTCAAAGCTGGAATTGTAAATATAG

AGAAAAAGAAGGATGTTGTTTATTCTTGAAAGAGTATAATTTTACTTC

TAGCAACTCTCCCACTTCGCTTGACTTCATTTATTTCTTGGGCACATAG

GCGTAGTAATCTAGACCAACAGATAATTTGCCGGAATGATATAGCGATT

GGAAAATGAACTGAAATTTTTTGCTGTCTTTCAATTTGACGGGCAGTTC

ATCAGTGACCGACCATATAAATACGTTGAGAATGTTATTCTTCCTCGTA

GTTGAAGTGGCTTCATAATTTCAGAACTCAATAGATAAACTAGGATGTT

TTAAAGCAATTAATGCTCACAAGTAAGGAGCGACTCTCTTGCTTTTCGA

ATACTAAAAGTATCGTCCCAACCCAGAAAAAAAGACCTCTTAACTGCAA

AATAAACTCTATATATTTCTTCTAAAACAGTTTCAGGTTGGATAGTATC

GCATTCTCATCACTTCTAACTAGTAGGCCATGAGATATATTAACGTTTA

CTTGAGTTCTAAGTTCTCCGAATTAGATGCACAGCACAAACAAGATTAG

-continued
GTTTCACTTGGTACAAAATACGAACAGAGTTTAAGGTCGTAATTTCATT

TCGTTATTGATCCCCACAATCTATTCTTATCACAGTCATCAGATAGTCG

CGAAAAAGCATGCAGAAAAGGGGGTCGTCCCTATCTAAGTTGTAGCATT

ACAACAAATATGACTACACTCAGTGTCGCAATCGGTATAGCCAACGCTG

CAAAATGGATTCTACTGAGAATGGTATGATGATCCCAGGATCAATTTCC

CAAAAATTAAAAAAAGTAAAATAAAAAGCATCAGATATTAGGGAGGTGG

TAAGATTGCTCTGCAAGCGATCACGAGATTTTAGGTTTTCCTTTATGTA

CTATATAAAGCGCAGATTGGATGCCGCTTTTCCCTCCTGGGCTATGATA

ATATAGCGAACGAAATACACGCCAAAATAAA pSD003-SEQ ID NO: 3
TCACATTCATAGCATCTCTCGCCTGCAATAGCTTCCACGATAGGAATAT

CTGTGAAAGTGAACATGCTATTTCGATGATATAAGACTTTAAGATCTGG

CATGTTTGTGTTGGAGGTTACCCTGGGGTCAATAACCCTAATTATCTCC

TTCACTAAAAATGATGAAGATTCTTCGGATTCGTTTTTGAACAGAGTTA

ATGCCATTTCTTCGTCAATAGAAAATCAATATCTGGTATCTCATCTTT

TACATATTGAGGATTTAGTTTTCTTCCCTTTGGATAGTACATTATGATC

AATGTATTCCTGTCTTTATTGATAAAGTATTGGCATTCTGCTTCTTGTA

CACCTTTGAATTGTTTGTCTGGAAGTGACTGACATTTTTCCACATTGCT

AACGGTTTGGCACGAATTACATCTAAATAAAATGTCTTCTCCGGATTCG

TGTATTAAGTGATACTCCAATGATAAATCCCCACCTATCGAACCAGAAT

CGGCATTGGCCACAGTCACAGGTAACTTTAGGTCTTGAAAAATCCTTCT

ATAGGCTTCATTGACATTGTCATAAGACTTAAGACCATCTTCTTTGGTC

AAGTCAAAAGAATAGGCATCTTTCATGAGAAACTCTCGTCCTCTCAACA

AACCTCCCCTAGGTCTCAACTCATCTCTATATTTGCGGGAAATTTGGTA

CACGAGAAGGGGTAAATCTTTATATGACGAACATAAGTCACCAACTAAG

TTTGTGATTTCCTCTTCACAAGTTGGCACTAAACAGTAGTCTCTATCCT

TGGAGTCTTTGAACTTGAACAATTCATTGTTGTCCCATCTCTTAGTTCT

CTCCCATAAATGCTTGGAAGACAGGCTACTTAATTCCATTTCCAGCCCA

CCAGCCTGATCCATTCTTTTCCTAATTACATTTTGAAGCTTTTTATAGG

TACGGAGTCCTAATGGAAGCCAGTGAACTATTCCTGCTGCAGGCTGGTA

AATAAACCTTGATTGAAGGAGCATATCATGAGTAGTAAGGTCCTTTACA

GAAAATAGTTTACTTCCTTGAAGAGAAGTAGAATAAAACCTCATGTTGG

GTCTCCATGAAAGGTTCAAAGGCATTGATCCTTTAGGTACTTCAGGATG

TTTAAGTCATCAAACTGTCCATCAAAGGTAGTATAGTATTTACCATCTA

GATAGTGATGTATGGGTGTAACACAACATTTAAATGTTGTAAATTAACA

TTAGGACTGAGTCCGGAGATGCTATTGTCACCTAAATCTATTAGAAAGC

ACTTCAGTTATATCATCGATAGAGGTTTGAAGATAAACCTATTGTTGAT

AAATAACCCCATTACCCGTTTACGTAGCAAGGTTCAAAAATTTGCTTAG

ATCGGAGCTAAAAATTCGACTGACTTCTTTCGAAAATGTGGATTATGCA

AGCAACGTTGCTATCGGAATAGTATATAAGGTCGATCTGCCCCATTACA

AATTGTAAAGCAACAAACATCCTACGCAAA pSD004-SEQ ID NO: 4
TCAGTTTCACGGTTATGTGAGCTGTCTCCGCGTGAGGCAGTAACCTCTG
TGTCATGGATACAGGCTGGTACACATTTGGCAGTAGGAACACAATCTGG
TTTAGTTGAAATATGGGACGCCACGACGTCCAAATGTACAAGATCAATG
ACTGGGCATTCGGCCCGAACCTCAGCGCTGAGTTGGAACCGTCATGTTT
TGAGTTCTGGTTCAAGAGATCGCAGTATCTTACATCGGGATGTACGTGC
AGCAGCTCACTATACAAGTCGCATTGTTGAACACCGCCAAGAGGTTTGT
GGCTTACGTTGGAACGTGGATGAAAACAAGCTGGCCAGTGGTTCCAATG
ATAACCGTATGATGGTATGGGATGCACTGCGTGTAGAACAGCCCCTTAT
GAAAGTTGAAGAGCATACTGCGGCTGTTAAGGCGTTGGCATGGTCACCT
CATCAACGTGGAATACTGGCTTCGGGTGGAGGTACTGCTGACAGACGTA
TCAAGGTGTGGAATACTTTAACAGGATCCAAGCTGCACGATGTTGATAC
TGGATCTCAAGTTTGTAATCTCTTGTGGTCTCGCAATTCTAATGAATTG
GTAAGTACTCATGGATATTCTCGAAACCAAGTCGTTATTTGGAAATATC
CGCAAATGAAGCAACTAGCATCTTTGACTGGTCATACTTATCGAGTCCT
TTACCTTTCCATGTCACCTGATGGAACTACAGTCGTAACGGGGGCTGGA
GACGAAACTTTAAGATTTTGGAACTGTTTCGAGAAGTCACGACAAAGCG
GAGGAGGATCAATATTACTAGACGCTTTTAGTCAGCTTCGTTAAATTAC
CACCAAATTTGGTGCAAAAGGGCCCATATGGTGCTACAACCAAAGGAAC
TTTCTAATTTTGATAATGATGTCATTTCTCTCATCGGGATGAAAATAGA
AGTCGAAAGGATTTTTGTCACTATTTCAAGCCCCACCTGCAGCTGGCAG
CATTTCTATTGTTTATGCATTGTCATTTATGGGAAAACTAAGAAAGTTC
CTCTCCACCCGGACTCCACTGGTAAATATGCGATATCGGAATCATGACC
AACCCATATTTTGATCCTAATCATTTCGGTTCTAGTCTCCGATCGGACT
CCGTAAAACTGCGGAGTGAACTCCAACGGAGAATACTGCAGCCAATCTC
ATATTTCATTTGTTATTTGTCCCTCAACTGTCTCGATAAGGTCATCTGT
GTTTGACTAGATGTTCGTCATTGGCATGTCAAACAAGGCTAGACCTTAC
AATCATCTCTTACGAATGTAAGTGAATGTAACTATATTTTCCTTGCTAC
TTTAACGAGGTTAACCAACCCCGCACATCCCCACACCACCGCTCTTGA
TAAGCATCTCCGAAAATGCATGACGCGACAACTTCAAGCATGTTGTATT
TACTGAGTTTTCAGCCTCACTATCGATACCTCTATAAATAGAGGCACTT
TCGTCTCTTCTCCCTCCCCACAAGAAACCA pSD005-SEQ ID NO: 5
AGAAGTACTGTTATGAATCGATCGACGTGACATGTTGTTGATGGTTCTG
ACTTCTTGATGTCCGCGTTTTCTGTCTCTCAATAGTGGTGTTCGGGGGA
AGTATGGTTCTAATACTTAACAGGTAAGATGGTTGCAATGAGCACCTGG
TAAAGCAACTTGAATTTCCTGCCCTGTCTCCGTTAAGTTATATTCGACT
CAAGGTCCTTGCTTCCTGTCTGTTCTGTAAAACTTCCCTTTGGTGTCTT
CTATATCAACTTTAAAAACAAGGTAGTGTGTCGAGCGATAGTACTGTGT
CTTTTTCCCTATGAAAAAAATCGCACCATCCAAGACTTCTCACCTTCAA
CAGCTTCAACATCATGTTCGGTCCTTTTAGAGCTACGCTGGTCGATCTA
GGAGGTCTGCTATGGAAACGTCCTTGGAGAATGTCCAAACCACAGAAAT
ATAGACTCCGCAAAAGAATGCAACTTGTAGACTCCAATATCGACATTAT
TTACCAGGGACTGACTGAGGAGGGTCTGTCTTGCAAAGTGATAGATAAC
TTGAAACAAAACTTCCCAAAGGAGCATGAAGTGCTCCCCAAAAACAAGT
ATACCGTGTTTAACAAGACAGCCAAAAACTATAGAAAGGGTGTTCATTT
GGTTCCAAAATGGACCAAGAAGTCTTTGAGAGAGAACCCCGAGTTCTTC
TAATTGCACATTTCTTCCTGTTCATAGATTATCCCACACATAGTTGCTC
ACAAAAAAATCACTATAATTTTCCTCCACCGGCAGTATATCACTAACAC
CTTTATCTTTATTGTAGATTATAATCTGATCTTTATCCTTAGATGTATC
TATCATCAACCCCATGCTCTTGAAAAGCTTGAGTCTTAACACTGTCGAA
TCGTAGTTTTCTTGTAGATCATTCGATATCACTGCTTTTTCTTGCTCTT
CTAATTCGTTGAGATTCTGGGTCAAACTAGAGATTGAATTCTGAAGGTG
ATTCATGTTCATCTCCAGATCTGTTATTGATTTTGCTAATTTAAATTTT
TCGTGTTCAAGCTCTTCGATACTCTTTAGGGTCTGTTGACGGTCTTCTG
TTTCCAATAATTGCTTGTTGAACTCTTTAAGTTCGTCTCTCTGTTTACT
GATACGTGACAACAAATCTAGCTGGTGATCGAGTTTAAGTTTCCGTTTG
GAGCTCAACAGAGAAAGATTTTCATTAATTTGGTTGATAGTTTGCACGT
CCGGTTCGATCTGAAAATTCTCTATAGTCGACCTGATTAAGGACACAGT
CTCTTGAAGATCGGACATTGGATTTATGGAGAAGGGAGATCAAAGCGGA
ACCAGTTGCACTGTTTACCTTTCCAGTCGAGATACTTATCCCACAGGGC
CCTCACTTTCCAGGCAGAAGTCACCTAGGAGGCGCATCCCTCCGTTTGC
TTCCCTCGCGACAAACTCCCCTGTAAAAGAAAACTTCACTGAATCGTAC
ACCTAATCATACGACACTAACACAGATATA pSD007-SEQ ID NO: 6
GTCCTTTCCAAATTTTTGGTTGAAGGCATCGCTTAAATTATGAGCAGGA
TCGGTGGAAATAAGCAGGTATTTCTTGTTAGGATTGTGAAGGGCAAGCT
GGATAGATATAGAAGAAGATGTCGTGGTTTTACCGACACCCCCCTTACC
TCCAACAAAGATCCACTTCAGCGATTCGTGGTTCACAATTGATCGCAAA
CTTGGCTCTGCCTCAATATCCATGGTTGATGTCTAGTTGAGTGGCGTTT
GTGGTCTCTTGATGAGTTCAAGGCGAAAGAATATGATAGGAAAGCATGG
TTTGAACTTTTCGCGAAAGAAGGAATACTGTTCCGCGAGAAACTCCCCG
GTGCCAGAACCTTCCATTGAGGTTAATCGGTGGGAGGTGTTCGAATGAC
AATGTCAGACAAGGCGAACACGTCTTGTGACACCAGCTGGACTAAGAAG
ATTCGGTATGCACCGAAGAAGAAGGCCGTGTCTCAATTGGCAACTTTGC
AACAAACTACGGAGGAAAAGTCTCACAAGCTTTTAACCAAGTTGAATCA
CGACGACAACGATAAAGAAATCCTCAACCATCTAACACATGAAGTACAA

AGTAGAAATGTGATCTTATTGGACAAACTAGAGGAGCTCAACAAGGAAC
TGGGCTGGATTAAAGACCGAAAATGAGGAACCATGAGCACTGGGCGTTT
CCAGAAAAACTGCAACCAACGATGGGAAAATGATACCACACTACTATGG
TCACCCCACATTGTGAAATTTCAAACCAAAAAGATCAACCCCATAATT
CCCCAGAGGGTTTTCCCAACAATTTTCCAACGGACTTGATAATGAGTCA
GATCATTTGAGCATATTCATCTTACCCCTTATTCCGTGACAATTTACCT
ATTCCATTCAAAGCATACGGTATCCCGTGACCTTCTCATGGAGATCATT
CTCCACCGATACAGCATATACACAGATATACCCAACTAATATCAATTGG
ACCTTGATATGGTCGACCTTGATGGTCCCGTCCAACCTTAAAACTTAGT
TTAATGCTATACTTTCGCCTTGAACCAAATCTGTCTCCCCCTCAATCAT
CTCTATGCAAGAAGGTCAACACTGATTACGTGAGCAACAGCCAGCAATC
GTTCGAGTCCCCGCCAAAAAGGCGGAGTTACTGCTCCTTGTGACCACA
CCCCCTGAGACCACGTCCCTAAACGATCCTTGTCGGTTCCTTCGTCCAA
TTGGCAATTGCCACGCATACGTGAATCGTTATTGTTTCGCCTACCTTGC
GTCATTCGTTCCAGAATGTTCGACATACTCCTCTAGAACATACCGTCAC
ACCACCATCTTAAGTTATCTTCACGTGACCATGACGTACATTGTAGTTG
ACTACCCCATTCTCATCATTCCGATGCGGCCAAAAATCTCTATATAAAG
ACCGTATCCCCTAATATTCTCTTCTTGTTAAGACATTAACTTAGTTAAT
TCACCAATTACTCACTTATAAACAAACAAA pSD008-SEQ ID NO: 7
GTTTCTCTTGGGGAGATACTTTTTTCGCGTGCTCCTCCGTGCGGAACTT
CCTTCTGAGCTTCTACCTCTCAGATTAGTCTAATCGCATCAGGAATAAG
ACTGAGAATGCTTTTAAGGAGAGGCTTGAGATTGGCTAATTGCGTTCCG
AAGTACTCTTTCAAAAGGAGTTATACCCCTCTCAACTACGATTCTCTAA
AGAATTATCGTAGGCATGCTCAGGCGCCTCAACCCCATCAGTTTGACGC

CACTAGATGGGACCAACAACCAGTTACTAATGAGCAAGGAGTAATACTC
CCATCCGACTCAATTGCAAACATTCTGAGACAACCAACTCTGGTCATAG
AACGGCAAATGGAAATGATGAATATATTTTTAGGATTTGAGCAGGCGAA
CCGATATGTTATCATGGATCCTACAGGAAGTATTTTGGGTTACATGCTA
GAAAGGGATCTGGGCATCACCAAAGCTATATTGAGACAGATCTACCGTT
TGCATCGACCTTTTACAGTGGATGTAATGGATACTGCAGGAAATGTATT
AATGACAATCAAGAGGCCGTTTAGTTTCATCAATTCGCACATCAAAGCT
ATATTACCCCCTTTCAGGAACAGCGACCCAGACGAACATGTAATTGGAG
AATCCGTTCAAAGCTGGCATCCTTGGAGACGAAGATACAATCTATTTAC
AGCACAAATTGGCGAAAAGGACACTGTCTACGATCAGTTCGGGTACATT
GACGCACCGTTTCTTTCCTTTGAGTTTCCTGTACTTTCAGAATCTAGGC
AAACGCTAGGTGCTGTCTCTAGAAACTTCGTGGGCTTTGCAAGAGAGCT
TTTCACAGATACAGGAGTTTACATCATCCGTATGGGGCCTGAATCTTTT
GTAGGGCTAGAAGGGAACTACGGGAACAATGTGGCCCAACATGCCCTTA
CGCTGGACCAAAGGGCTGTATTATTAGCCAATGCCGTTTCAATTGACTT
TGATTACTTTTCTAGGCACTCGTCACACAGTGGTGGCTTCATTGGGTTT
GAGGAATAGACAGGGTCTCGTCAACTCAGCTCCTGCCACCAAACCAATC
ATTGATCAACGAGCACACTTTTGTCCACGTGAGATCGCTTTCGCTTGCA
GAAAGAGCAATGCATGAAAACGGCAAACGCAAACGAGCAAAAAACGA
GTAAATAACTACAATTTCACCACCAACAGGGTCAAAGAGCTTTTGAGAC
ACTATAAAAGGGGCCCTTTCCCCCCAGGTTCCTTGAAATCCTCATTCAA
TTATGTTTTTTACTCATAATTTGACTCAATTGGCATCTTCTTCTTTGTT
CATATACAGTAATTGATATGACGCTTAGTCATTATTAGTGTTCTCGACT
AGCAGTGGCGAAAAAGGGGAGTTATTTTCTAGAACCGACCGCAAACT
ATAAAGAAAGCTGCCCCTCATATACCTTTCGAATTCTTTATTTTCTGT
GTTTCTTCCCTATTTAACATCTACACAAAA

What is claimed is:

1. An isolated nucleic acid sequence having at least 90% sequence identity to the full length of any one of SEQ ID NO: 1-6 operably linked to a gene encoding a protein that is heterologous to *Komagataella phaffii* (*K. phaffii*).

2. The isolated nucleic acid sequence of claim 1, wherein the protein is an enzyme, a peptide, an antibody, or a recombinant protein.

3. The isolated nucleic acid sequence of claim 2, wherein the enzyme is a lipase, amylase, xylanase, protease, glucoamylase, glucanase, mannanase, phytase, or cellulase.

4. The isolated nucleic acid sequence of claim 1, wherein the protein is glycosylated or non-glycosylated.

5. The isolated nucleic acid sequence of claim 1, wherein the protein comprises disulfide bonds.

6. The isolated nucleic acid sequence of claim 1, wherein the nucleic acid sequence is 50, 100, 200, 300, 400, 500, 600, 700, 800, 900, 1000, 1500, 2000, 3000, 4000 or 5000 bases upstream from a translational start site of the gene encoding the protein or any number of bases in between a range defined by any two aforementioned values upstream from the start site of the gene encoding the protein.

7. The isolated nucleic acid sequence of claim 1, wherein the isolated nucleic acid sequence drives expression of the protein in a yeast cell in the absence of methanol, and wherein the expression of the protein is up to 40 g/l.

8. A vector comprising the isolated nucleic acid sequence of claim 1.

9. The vector of claim 8, wherein the vector is a yeast integrative plasmid, episomal plasmid, centromere plasmid or artificial chromosome.

10. The vector of claim 9 wherein the vector comprises a selectable marker.

11. A yeast cell comprising the isolated nucleic acid sequence of claim 1 or the vector of claim 10.

12. A method of expressing protein in a yeast cell comprising:
   providing a yeast cell;
   introducing the isolated nucleic acid sequence of claim 1 into the yeast cell;
   fermenting the yeast cell under at least one fermentation condition in the absence of methanol in a nutrient broth;
   harvesting the yeast cell;
   and recovering the protein from the yeast cell.

13. The method of claim 12, wherein the isolated nucleic acid sequence is comprised within a vector.

14. The method of claim 12, wherein the protein is excreted or is intracellular.

15. The method of claim 13, wherein the protein is an enzyme, a peptide, an antibody, or a recombinant protein.

16. The method of claim 15, wherein the enzyme is lipase, amylase, xylanase, protease, glucosamylase, glucanase, mannanase, phytase, or cellulase.

17. The method of claim 12, wherein the method further comprises driving expression of the protein.

18. The method of claim 12, wherein the yeast cell is a species of methylotrophic yeast.

19. The method of claim 12, wherein the yeast cell is of the genus *Komagataella*, and the yeast cells are selected from the group consisting of *K. farinose, K. anomala, K. heedii, K. guilliermondii, K. kluyveri, K. membranifaciens, K. norvegensis, K. ohmeri, K. pastoris, K. methanolica, K. phaffii* and *K. subpelliclosa*.

20. The method of claim 12, wherein the nutrient broth comprises at least one carbon source.

21. The method of claim 20, wherein the at least one carbon source is selected from a group consisting of dextrose, maltose, glucose, dextrin, glycerol, sorbitol, mannitol, lactic acid, acetate, xylose, or other partially hydrolyzed starches, and any mixtures thereof.

22. The method of claim 20, wherein concentrations of the at least one carbon source varies from 0.5 g/L, 1 g/L, 2 g/L, 4 g/L, 6 g/L, 8 g/L, 10 g/L, 11 g/L, 12 g/L, 13 g/L, 14 g/L, 15 g/L, 16 g/L, 18 g/L, 20 g/L, 22 g/L, 24 g/L, 26 g/L, 28 g/L or 60 g/L or any concentration within a range defined by any two aforementioned values.

23. The isolated nucleic acid sequence of claim 1, wherein the nucleic acid sequence drives expression of the protein in a yeast cell in the absence of methanol.

* * * * *